(12) United States Patent
Chen

(10) Patent No.: US 7,312,865 B2
(45) Date of Patent: Dec. 25, 2007

(54) METHOD FOR IN SITU MONITORING OF CHAMBER PEELING

(75) Inventor: Yi-Ling Chen, Taichung (TW)

(73) Assignee: Taiwan Semiconductor Manufacturing Co., Ltd., Hsin-Chu (TW)

(*) Notice: Subject to any disclaimer, the term of this patent is extended or adjusted under 35 U.S.C. 154(b) by 241 days.

(21) Appl. No.: 10/813,799

(22) Filed: Mar. 31, 2004

(65) Prior Publication Data
US 2005/0219520 A1    Oct. 6, 2005

(51) Int. Cl.
*G01N 21/88* (2006.01)
(52) U.S. Cl. ..................... 356/237.2; 356/72
(58) Field of Classification Search .. 356/237.1–237.2, 356/72, 311–316, 437; 216/60, 67; 438/706–707, 438/9; 156/627.1, 345
See application file for complete search history.

(56) References Cited

U.S. PATENT DOCUMENTS

| | | | |
|---|---|---|---|
| 4,263,088 A | 4/1981 | Gorin | |
| 4,312,732 A | 1/1982 | Degenkolb et al. | |
| 4,493,745 A * | 1/1985 | Chen et al. | 438/9 |
| 4,496,425 A | 1/1985 | Kuyel | |
| 5,226,056 A * | 7/1993 | Kikuchi et al. | 373/18 |
| 5,288,367 A | 2/1994 | Angell et al. | |
| 5,347,460 A | 9/1994 | Gifford et al. | |
| 5,552,016 A * | 9/1996 | Ghanayem | 156/345.25 |
| 5,658,423 A | 8/1997 | Angell et al. | |
| 5,759,424 A * | 6/1998 | Imatake et al. | 216/60 |
| 5,807,761 A | 9/1998 | Coronel et al. | |
| 5,810,963 A * | 9/1998 | Tomioka | 156/345.28 |
| 5,877,032 A | 3/1999 | Guinn et al. | |
| 5,897,378 A | 4/1999 | Eriguchi | |
| 5,910,011 A | 6/1999 | Cruse | |
| 5,986,747 A | 11/1999 | Moran | |
| 6,024,831 A * | 2/2000 | Hwang et al. | 216/59 |
| 6,046,796 A | 4/2000 | Markle et al. | |
| 6,057,247 A | 5/2000 | Imai et al. | |
| 6,071,828 A | 6/2000 | Mihara | |
| 6,153,115 A * | 11/2000 | Le et al. | 216/60 |
| 6,157,867 A * | 12/2000 | Hwang et al. | 700/121 |
| 6,235,655 B1 | 5/2001 | Jozaki | |
| 6,242,350 B1 | 6/2001 | Tao et al. | |
| 6,267,121 B1 | 7/2001 | Huang et al. | |
| 6,277,763 B1 | 8/2001 | Kugimiya et al. | |
| 6,355,570 B1 * | 3/2002 | Nakata et al. | 438/706 |
| 6,395,563 B1 | 5/2002 | Eriguchi | |
| 6,419,846 B1 | 7/2002 | Toprac et al. | |
| 6,429,141 B1 | 8/2002 | Van Ngo et al. | |
| 6,492,068 B1 | 12/2002 | Suzuki | |
| 6,492,186 B1 | 12/2002 | Han et al. | |
| 6,635,577 B1 * | 10/2003 | Yamartino et al. | 438/706 |

(Continued)

*Primary Examiner*—Sang H. Nguyen
(74) *Attorney, Agent, or Firm*—Duane Morris, LLP

(57) ABSTRACT

A method for in situ monitoring of particles generated by a reaction by-product film peeling from an interior wall of a reaction chamber of a semiconductor fabrication apparatus to determine reaction chamber condition. The method includes the steps of: exciting the particles to emit light; and comparing an intensity value of the light, measured at a selected time during a predetermined time period, to a predetermined light intensity threshold value. If the intensity value of the light measured at the selected time is above the predetermined light intensity threshold value, the chamber condition is abnormal. If the intensity value of the light is equal to or below the predetermined light intensity threshold value, the chamber condition is normal.

16 Claims, 4 Drawing Sheets

U.S. PATENT DOCUMENTS 6,815,362 B1 * 11/2004 Wong et al. ................ 438/706
7,006,205 B2 * 2/2006 Agarwal et al. .............. 356/72
2002/0192845 A1 12/2002 Nguyen et al.

* cited by examiner

METHOD FOR IN SITU MONITORING OF CHAMBER PEELING

FIELD OF THE INVENTION

The present invention relates to semiconductor manufacturing, and more particularly, to a method of in situ monitoring of particles generated by a reaction by-product film peeling from an interior wall of a reaction chamber of a semiconductor plasma etching apparatus.

BACKGROUND OF THE INVENTION

Over the last several years, plasma etching has increasingly replaced wet chemical etching in the fabrication of integrated circuits and semiconductor devices. Plasma etching is a dry etch process that is typically carried out in a metal reaction chamber. During the plasma etching process, a gas is pumped into the reaction chamber and is excited by a radio frequency generator to a plasma state. The plasma generated in the chamber may be used, for example, to etch a thin metal film on a semiconductor substrate.

During the plasma etch process, reaction by-products adhere to the interior wall or walls of the reaction chamber. After a certain period of time, the adhering reaction by-product film randomly peels off from the interior wall or walls of the reaction chamber, thereby generating film particles in the chamber. If the concentration or density of these particles stays below a certain threshold value, i.e., which is considered a "normal chamber condition", the semiconductor wafers processed in the chamber are not negatively effected. If, however, the concentration or density of these particles exceeds the threshold value, i.e., which is considered an "abnormal chamber condition," the semiconductor wafers processed in the chamber can be negatively effected, as the high particle concentrations in the chamber can cause defects in the semiconductor structures being formed on the wafers.

One existing method for monitoring the concentration of particles generated in the reaction chamber by peeling reaction by-product film, is to perform an off-line particle monitor. This method involves periodically placing a blank semiconductor wafer in the reaction chamber and operating the chamber according to a preset process or recipe similar to an actual wafer production recipe including the use of a flow gas, servo pressure, and RF power. The wafer is then removed from the chamber and the number of particles deposited on the wafer is counted. If the number of particles on the wafer exceed a certain value, an abnormal chamber condition exists and a maintenance cleaning must be performed on the chamber to remove the adhering film that is peeling off from the interior wall or walls of the reaction chamber to provide normal chamber processing conditions.

Another method presently used for monitoring the concentration of particles generated in the reaction chamber by the peeling film, is to perform a periodic defect inspection using a defect inspection tool to scan product wafers directly after they are removed from the chamber. This process takes a considerable amount of time to perform. Since the time during which the inspection is taking place is used to process additional semiconductor wafers, this process does not provide and "immediate" indication of an abnormal process chamber.

Thus, a major disadvantage of both of the above methods is that they are both performed while additional wafers are still being processed in what could be an abnormal process chamber. If an abnormal reaction chamber condition is detected, typically, many wafers have already been processed under these abnormal chamber conditions, which may cause defects in the semiconductor structures being formed on the wafers. Additionally, because of the randomness of the film peeling, these test methods may not always be needed. If the chambers are not utilized during the performance of the test method to avoid the possibility of making defective products, and the test indicates a normal chamber, the downtime decreases the utilization of the etching apparatus.

Accordingly, what is needed is a method for in situ monitoring particles generated from reaction by-product films peeling from the interior wall or walls of a reaction chamber of a plasma etching apparatus.

SUMMARY

A method is described for in situ monitoring of particles generated by a reaction by-product film peeling from an interior wall of a reaction chamber of a semiconductor fabrication apparatus to determine reaction chamber condition. The method comprises the steps of: exciting the particles to emit light; and comparing an intensity value of the light, measured at a selected time during a predetermined time period, to a predetermined light intensity threshold value. If the intensity value of the light measured at the selected time is above the predetermined light intensity threshold value, the chamber condition is abnormal. If the intensity value of the light is equal to or below the predetermined light intensity threshold value, the chamber condition is normal.

DETAILED DESCRIPTION OF THE INVENTION

The present invention is a method that utilizes Optical Emission Spectroscopy (OES) to in situ monitor particles generated by peeling of a reaction by-product film from an interior wall of a reaction chamber of a plasma etching apparatus.

OES is a well known process whereby the wavelengths present in the light emitted by a material during a chemical and/or atomic reaction are analyzed so that the properties of the material can be determined. During a plasma etching process, a plasma is generated to etch semiconductor wafers. The atoms and molecules in the plasma are excited and emit light when their electrons change energy states. Because each of the species in the plasma emits a unique spectrum of light, OES can provide certain information about the etching process, such as the progression or end point of the etch process. For example, the intensity of the various spectral lines present in the light can be used to identify the presence of certain species within the reaction chamber of the plasma etching apparatus.

In the present invention, OES is used during a waferless autoclean cyle for analyzing the wavelength of light emitted by peeling reaction by-product particles within the reaction chamber of the plasma etching apparatus, to determine the density of the particles in the chamber. If the density of the particles exceeds a predetermined threshold known to cause defects in semiconductor wafers processed by the apparatus, the reaction chamber requires a maintenance cleaning. The OES method of the invention may be practiced with any plasma etching chamber that provides a means through which light present within the chamber may be spectroscopically observed.

Figure 1:
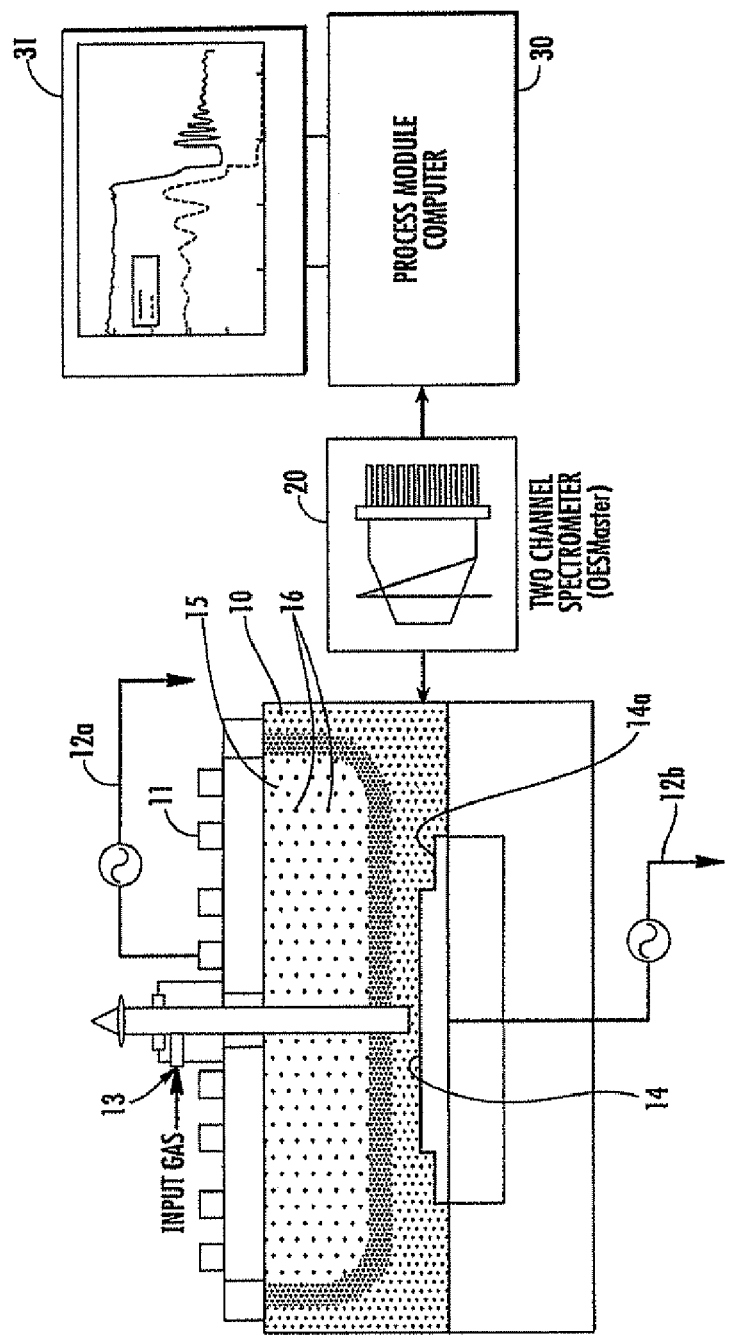
FIG. 1 is a diagrammatic sectional view of a plasma etching apparatus which may be used for practicing the method of the present invention.

An exemplary plasma etching apparatus for practicing the method of the present invantion is shown in FIG. 1. The apparatus comprises a reaction chamber 10, which may be made from a metal, and an optical emission spectrometer 20. The reaction chamber 10 may include a coiled transformer coupled plasma (TCP) electrode 11, powered by a high frequency RE power source 12a. The TCP electrode 11 may be disposed immediately above the reaction chamber 10 for generating an RF power inside the reaction chamber 10 during an etching operation when the TCP electrode 11 is powered by the high frequency RF power source 12a. One or mare gas inlet apertures 13 allow process gases to be pumped into the reaction chamber 10 and one or more gas outlet apertures (not shown) allow vacuum evacuation of chamber. A wafer stage 14 is disposed within the chamber 10. High frequency power is applied to a bias electrode 14a associated with the wafer stage 14 from a high-frequency power source 12b to generate a bias magnetic field inside the chamber 10. The reaction chamber 10 may be controlled by a computer 30 and a computer user interface 31. The computer 30 is conventionally adapted to implement various etching recipes in the reaction chamber 10 and process optical information received from the optical emission spectrometer 20 via the user interface 31. The optical emission spectrometer 20 is conventionally adapted to allow filtering of all wavelengths of radiation except the wavelength of light emitted by the particles 16, the wavelength filtering process being controlled by the computer 30 through the user interface 31. The reaction chamber 10 is configured to allow the optical emission spectrometer 20 to observe the interior 15 of the reaction chamber 10 to allow in situ monitoring of the light emitted by the RF excited peeling particles 16 in the reaction chamber 10. An example of such an apparatus for practicing the method of the present invention is sold by Lam Research Corporation under model number 2300.

As described earlier, OES is performed when the plasma etching apparatus is operated in a conventional waferless autoclean (WAC) cycle. Most plasma etching systems are adapted to perform a WAC cycle. The WAC cycle is a well known reaction chamber self-cleaning process that is routinely performed after each wafer has been etched.

Figure 2:
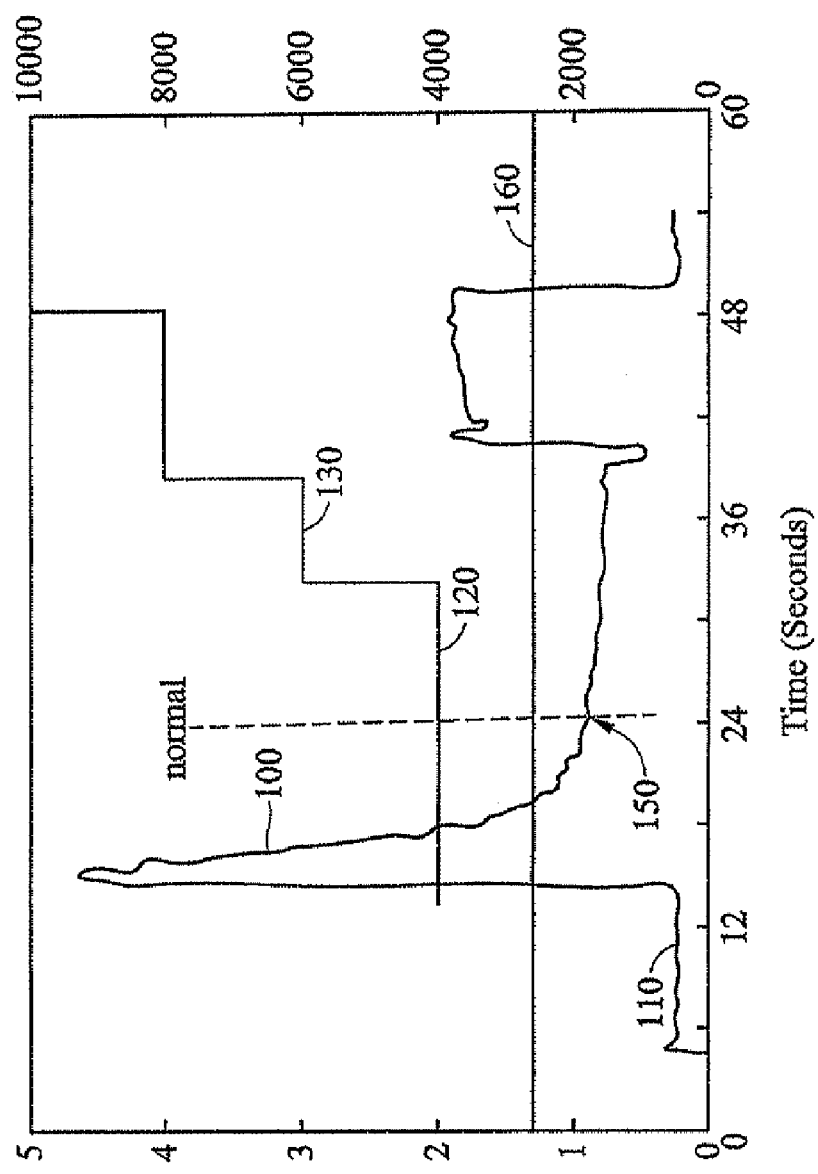
FIG. 2 is a graphical display, provided by a user interface, that plots time (x-axis) versus spectral light intensity of the particles (right y-axis) for a WAC cycle performed in a normal reaction chamber.

FIG. 2 shows a typical graphical display, provided by the user interface 31, that plots time (x-axis) versus spectral light intensity of the particles (left y-axis) and particle density (right y-axis) for a WAC cycle performed in a normal reaction chamber. The WAC cycle typically comprises a chamber stabilization stage 110, a first chamber cleaning stage 120, and a second chamber cleaning stage 130. Each stage of the WAC cycle is performed for a predetermined time period. In the chamber stabilization stage 110, the reaction chamber 10 is evacuated via the gas outlet, and a process gas, such as $O_2$ is introduced into the chamber 10 through the one or more gas inlets 13. The flow rate of the $O_2$ gas may be set to about 400 sccm and the pressure of the chamber may be set to about 8 mTorr. The chamber stabilization stage 110 may have a duration of about 10 seconds. In the first chamber cleaning stage 120, RF power is generated inside the reaction chamber 10. This may be accomplished by setting the TCP electrode RF power to about 1200 watts and the bias electrode RF power to about 8 watts. The flow rate of the $O_2$ gas may be maintained at about 400 sccm and the pressure of the chamber may be maintained at about 8 mTorr. The first cleaning step may have a duration ranging from about 20 to about 25 seconds during which particles, that may be contained in the chamber 10 as a result of peeling, are excited. The OES wavelength information is obtained from the excited particles during the first cleaning step of the WAC cycle. In the second chamber cleaning stage 121, a $Cl_2$ gas may replace the $O_2$ gas. The flow rate of the $Cl_2$ gas may be set to about 250 sccm and the pressure inside of the chamber may be set to about 22 mTorr. The TCP electrode RF power may be decreased to about 800 watts (the bias RF power is maintained at about 8 watts). The second chamber cleaning stage 121 is performed for about 10 seconds. It should be noted that other WAC cycles which are capable of exciting particles due to peeling can be utilized.

In accordance with the invention, the spectrometer 20 of the apparatus is set, via the computer 30 and user interface 31, to the wavelength of light emitted by the particles so that the spectrometer 20 measures only the light emitted by the reaction by-product particles generated by peeling. The RF power (generated within the reaction chamber 10 during the first cleaning stage 120 of the WAC cycle) excites the reaction by-product film particles which may be randomly peeling from the interior wall or walls of the reaction chamber 10. The spectrometer 20 measures the intensity of the light emitted from the particles and outputs a light intensity signal that is analyzed by the computer 30 and displayed on the user interface 31 as trace 100 in FIGS. 2 and 3.

Figure 3:
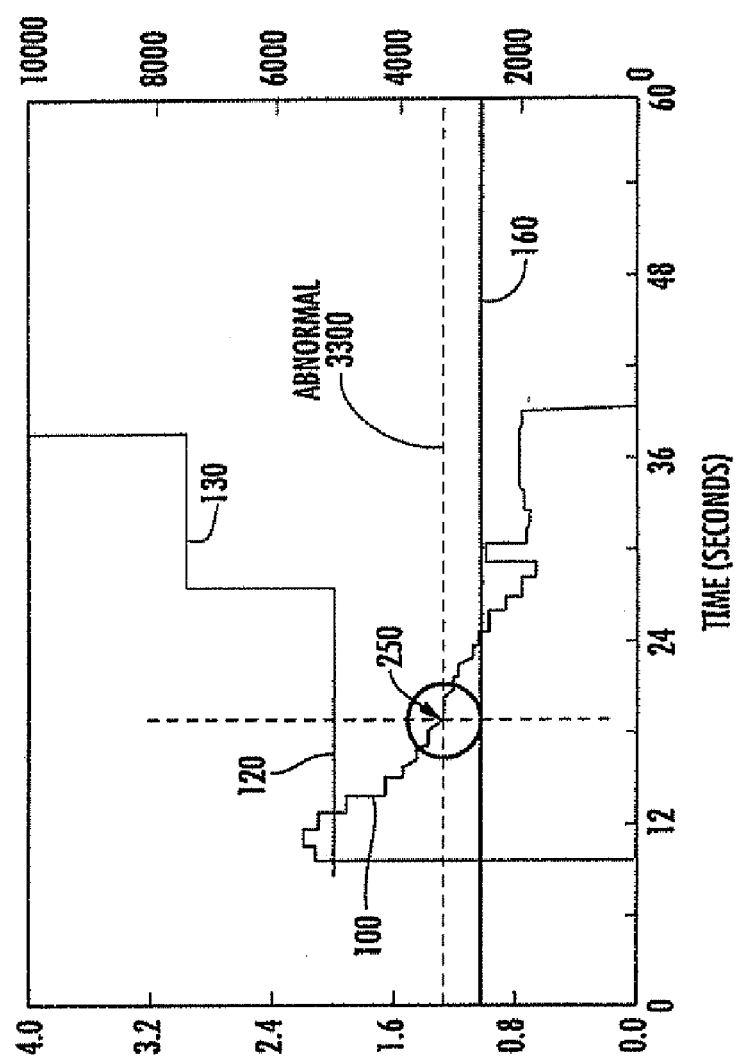
FIG. 3 is a graphical display provided, by a user interface, that plots time (x-axis) versus spectral light intensity of the particles (right y-axis) for a WAC cycle performed in an abnormal reaction chamber.

As the WAC cycle continues through the first cleaning stage 120, the light intensity (OES intensity) of the excited particles decreases with time, as indicated by trace 100 in both FIGS. 2 and 3. The horizontal line denoted by numeral 160 in FIGS. 2 and 3, identifies a predetermined OES intensity threshold level (e.g., about 2500) which equates to a peeled particle density that has been determined experimentally to be the upper limit of "normal". OES intensities below the OES intensity threshold level 160 equate to peeled particle densities within the chamber that are considered normal and OES intensities above the OES intensity threshold level 160 equate to peeled particle densities within the chamber that are considered abnormal. FIG. 2 demonstrates a normal chamber condition because the OES intensity value of the excited particles, as may be measured about half-way through the duration of the first cleaning stage 120 of the WAC cycle (broken vertical line intersecting trace 100 at point 150), is below the predetermined OES intensity threshold level 160. Thus, the quantity or density of particles peeling from the interior wall or walls of the reaction chamber is considered to be normal. On the other hand, FIG. 3 demonstrates an abnormal chamber condition because the measured OES intensity value is at or above the predetermined threshold (horizontal line 160), at about the half-way point 250 of the first cleaning stage 120 of the WAC cycle. Thus, the quantity or density of particles peeling from the interior chamber wall(s) is considered abnormal. When an abnormal condition is detected, the operator will not process any more wafers in the reaction chamber until maintenance cleaning is performed on the chamber.

One of ordinary skill in the art will recognize that OES may be performed during one or more other stages of the WAC cycle which operate to excite peeling particles in the chamber in a manner that can be monitored with OES. The OES intensity value of the excited particles, may also be measured at other times (other than at the half-way point) during the WAC cycle stage. In one illustrative embodiment, the spectrometer may be set to monitor light having a wavelength of about 703 nanometers, and the corresponding predetermined OES intensity threshold level or value may be about 2500. In other embodiments, the spectrometer may be set to monitor light having other wavelengths, depending upon the composition of the peeling reaction by-product film, and the predetermined OES intensity threshold may be set according to different product yield requirements and specifications. Further, it is contemplated that the OES method of the invention may be applicable to other types of semiconductor fabrication equipment, such polysilicon deposition chambers, to determine the relationship between abnormal/normal chamber conditions and OES intensity.

Figure 4:
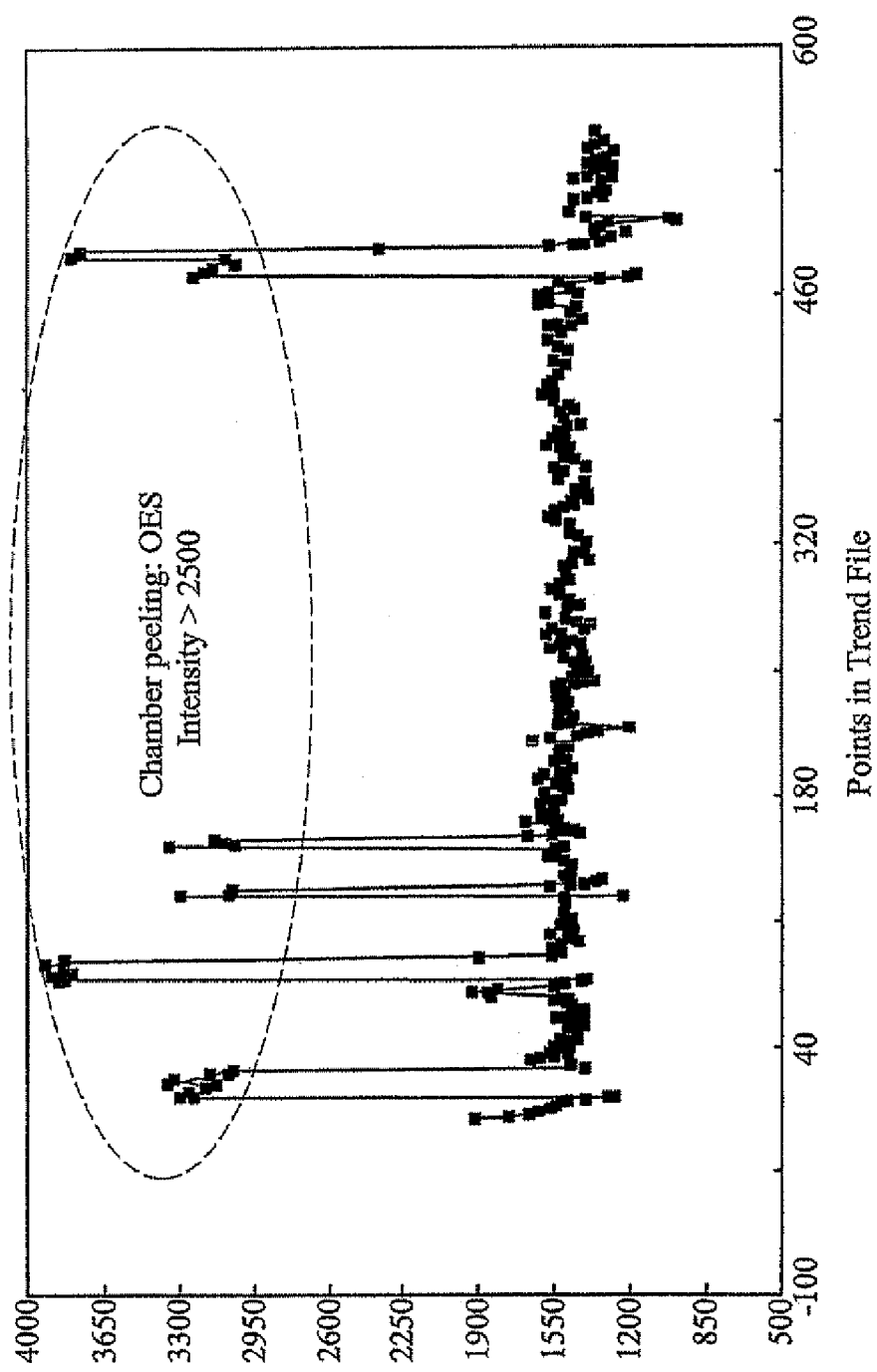
FIG. 4 is a density value trend file graphically displayed on a user interface.

In another aspect of the present invention, the computer may store each measured peeling particle OES intensity value in a trend file and graphically display all the OES intensity values on the user interface as shown in FIG. 4. The data obtained from the trend file may then be used later on for various purposes such as inline process control and the like.

The peeling particle OES measurements may be performed in real time, during the WAC process without performing off-line particle monitors and defect inspection scans.

It is to be understood that one skilled in the art may make many variations and modifications to that described herein. This and any other such variations are intended to be within the scope of the invention as defined in the appended claims.

What is claimed is:

1. A method of in situ monitoring of particles generated by a reaction by-product film peeling from an interior wall of a reaction chamber of a semiconductor fabrication apparatus to determine reaction chamber condition, the method comprising the steps of:
   operating the reaction chamber of the semiconductor fabrication apparatus in a cleaning mode to excite the particles generated by the reaction by-product film peeling from the interior wall of the reaction chamber of the semiconductor fabrication apparatus to emit light, the emitted light having a predetermined wavelength associated with the particles;
   measuring intensity values of the light emitted at the predetermined wavelength over a predetermined time period; and
   comparing the intensity value of the light, measured at a selected time during the predetermined time period, to a predetermined light intensity threshold value wherein if the intensity value of the light measured at the selected time is above the predetermined light intensity threshold value, the chamber condition is abnormal.

2. The method according to claim 1, wherein in the comparing step if the intensity value of the light is equal to or below the predetermined light intensity threshold value, the chamber condition is normal.

3. The method according to claim 1, wherein the selected time comprises about one-half the predetermined time period.

4. The method according to claim 1, wherein the exciting step is performed by generating RF power within the chamber.

5. The method according to claim 4, wherein the exciting step is further performed by pumping a process gas into the chamber.

6. The method according to claim 1, wherein the measuring step is performed by observing the emitted light with an optical emission spectrometer.

7. The method according to claim 1, where the semiconductor fabrication apparatus comprises a plasma etching apparatus.

8. The method according to claim 7, wherein the cleaning mode is a stage of a waferless autoclean cycle of the apparatus.

9. The method according to claim 1, wherein the cleaning mode is a stage of a waferless autoclean cycle of the apparatus.

10. The method according to claim 1, wherein the predetermined wavelength is about 703 nanometers.

11. The method according to claim 1, further comprising the step of storing the intensity value of the light measured at the selected time in a trend file.

12. The method according to claim 11, further comprising the step of graphically displaying the intensity value of the light stored in the trend file on a user interface.

13. The method according to claim 11, using data obtained from the trend file for inline process control.

14. A method of in situ monitoring of particles generated by a reaction by product film peeling from an interior wall of a reaction chamber of a semiconductor fabrication apparatus to determine reaction chamber condition, the method comprising the steps of:
    operating the reaction chamber of the semiconductor fabrication apparatus in a cleaning mode to excite the particles generated by the reaction by-product film peeling from the interior wall of the reaction chamber of the semiconductor fabrication apparatus to emit light; and
    comparing art intensity value of the light emitted by the particles, measured at a selected time during a predetermined time period, to a predetermined light intensity threshold value to determine the chamber condition.

15. The method according to claim 14, wherein in the comparing step if the intensity value of the light measured at the selected time is above the predetermined light intensity threshold value, the chamber condition is abnormal.

16. The method according to claim 14, wherein in the comparing step if the intensity value of the light is equal to or below the predetermined light intensity threshold value, the chamber condition is normal.

* * * * *

UNITED STATES PATENT AND TRADEMARK OFFICE
CERTIFICATE OF CORRECTION

| | | |
|---|---|---|
| PATENT NO. | : 7,312,865 B2 | Page 1 of 1 |
| APPLICATION NO. | : 10/813799 | |
| DATED | : December 25, 2007 | |
| INVENTOR(S) | : Yi-Ling Chen | |

It is certified that error appears in the above-identified patent and that said Letters Patent is hereby corrected as shown below:

Column 3, line 17, delete "invantion" and insert -- invention -- therefor.

Column 3, line 22, delete "RE" and insert -- RF -- therefor.

Column 3, line 27, delete "mare" and insert -- more -- therefor.

Column 6, line 47, delete "art" and insert -- an -- therefor.

Signed and Sealed this

Fifteenth Day of April, 2008

JON W. DUDAS
*Director of the United States Patent and Trademark Office*